United States Patent [19]

Kitamura et al.

[11] Patent Number: 4,500,727
[45] Date of Patent: Feb. 19, 1985

[54] PROCESS FOR PRODUCING METHYL LACTATE

[75] Inventors: Takanori Kitamura; Mitsuo Matsumoto; Masuhiko Tamura, all of Kurashiki, Japan

[73] Assignee: Kuraray Co., Ltd., Kurashiki, Japan

[21] Appl. No.: 359,414

[22] Filed: Mar. 18, 1982

[30] Foreign Application Priority Data

Mar. 23, 1981 [JP] Japan .................................. 56-42755
Jun. 19, 1981 [JP] Japan .................................. 56-95478
Jun. 19, 1981 [JP] Japan .................................. 56-95479

[51] Int. Cl.$^3$ ........................ C07C 69/68; C07C 67/03
[52] U.S. Cl. .................................. 560/179; 560/217; 560/233
[58] Field of Search ............... 560/179, 185, 233, 217; 568/454; 562/589

[56] References Cited

U.S. PATENT DOCUMENTS

| | | | |
|---|---|---|---|
| 3,896,047 | 7/1975 | Aycock et al. | 568/454 |
| 3,904,547 | 9/1975 | Aycock et al. | 252/414 |
| 3,996,293 | 12/1976 | Knifton et al. | 568/454 |
| 4,072,709 | 2/1978 | Tinker | 560/238 |

OTHER PUBLICATIONS

Riddick, John A. et al. *Organic Solvents*, at pp. 236–238, 276–280, 284, 289 and 290. (vol. II, 3rd Ed. of Techniques of Chemistry Arnold Weissberger, Editor.).
Craig, Lyman C. *Separation and Purification* at p. 302 (vol. III Part I of Technique of Organic Chemistry Arnold Weissberger Editor) (1956) Interscience Publ.
Berkman Sophia et al. *Catalysis* (1940) Reinhold, Publ. at p. 792.
Kirk–Othmer *Encyclopedia of Chemical Technology*, 2nd Ed. vol. 8 Interscience Publ. (1966) pp. 320–324 and 356–362.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

A process for producing methyl lactate by (I) hydroformylating vinyl acetate or vinyl propionate with a gaseous mixture of hydrogen and carbon monoxide in an organic solvent in the presence of a substantially water-insoluble rhodium complex and a tri-substituted phosphine to form α-acetoxy- or propionyloxy-propionaldehyde, (II) subjecting at least part of the reaction mixture obtained in step (I) to extraction with an aqueous medium to obtain an aqueous layer containing α-acetoxy- or propionyloxy-propionaldehyde and an extraction residue containing the catalyst components, and recycling the extraction residue to the hydroformylation step (I), (III) separating α-acetoxy- or propionyloxy-propionaldehyde from the aqueous layer containing the same as obtained in step (II), (IV) oxidizing α-acetoxy- or propionyloxy-propionaldehyde obtained in step (III) in the liquid phase with oxygen gas or an oxygen-containing gas in the presence of an oxidation catalyst to form α-acetoxy- or propionyloxy-propionic acid, and (V) reacting α-acetoxy- or propionyloxy-propionic acid obtained in step (IV) with methanol in the presence of an acid catalyst, and recovering the resultant methyl lactate by distillation.

10 Claims, No Drawings

PROCESS FOR PRODUCING METHYL LACTATE

BACKGROUND OF THE INVENTION

1. Field of the Invention

The present invention relates to a process for producing methyl lactate using vinyl acetate or vinyl propionate as a starting material.

2. Description of the Prior Art

Methyl lactate is used in significant quantities as a raw material for the production of lactic acid. Currently, lactic acid is commercially produced by the following route.

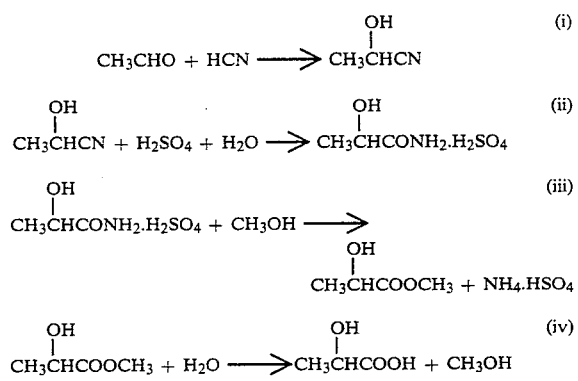

However, that method has the following disadvantages: (1) The starting materials, i.e., acetaldehyde and hydrogen cyanide, are likely to be less readily available and only at increased costs in the near future. (2) Hydrogen cyanide and its derivatives, which are highly toxic, must be treated by a costly process in order to dispose of the same to meet pollution control regulations. (3) Reaction (i) must be conducted at a sufficiently low temperature and the yield of the acetaldehyde cyanohydrin is not necessarily high. (4) Reaction (ii) is very exothermic and requires an effective cooling system which adversely affects the stability of the operation. The use of sulfuric acid at high temperatures necessitates the use of a reactor fabricated from expensive construction materials. (5) In reaction (iii), crystalline ammonium bisulfate which is difficult to work with is by-produced along with methyl lactate in equimolar proportions. Moreover, methyl methoxylactate, carbon monoxide, tarry substances, and the like are also by-produced in appreciable quantities. Though the formation of these by-products can be held within allowable limits by introducing large amounts of methanol and water into the reaction system, such a practice will result in increased energy consumption and, hence, an increase in the price of the final product. (6) In terms of overall yield, the yield of lactic acid is not necessarily high and large amounts of steam are consumed. Moreover, the method is not suitable for continuous production.

An alternative method has been proposed for the production of lactic acid which comprises hydroformylating a vinyl carboxylate to give an α-acyloxypropionaldehyde, oxidizing the same with oxygen to give an α-acyloxypropionic acid and finally hydrolyzing the same to lactic acid (cf. U.S. Pat. No. 4,072,709). However, this method has the following disadvantages. (1) In the initial hydroformylation reaction, the separation of α-acyloxypropionaldehyde from the reaction mixture is effected by distillation. However, (a) the α-acyloxypropionaldehyde undergoes decarboxylation, polycondensation, oxidation and/or other undesirable side reactions under the conditions of distillation, and (b) the repetition of hydroformylation followed by separation by distillation results in a loss in the catalytic activity of the rhodium complex recycled and reused and at the same time high-boiling by-products accumulate. (2) Since the α-acyloxypropionic acid obtained by oxidizing α-acyloxypropionaldehyde with oxygen contains impurities, the direct hydrolysis of the reaction product results in a lactic acid product of decreased purity. It is possible to purify the α-acyloxypropionic acid by distillation beforehand, however, because of its thermal instability, decreased yields of α-acyloxypropionic acid product are obtained. (3) The reaction mixture obtained by hydrolyzing α-acyloxypropionic acid contains, not only lactic acid, but also water, the organic carboxylic acid derived from the vinyl carboxylate used, and unreacted α-acyloxypropionic acid. It is difficult to recover lactic acid in high purity from such a reaction mixture. A need, therefore, continues to exist for an improved method of preparing methyl lactate in high yields.

SUMMARY OF THE INVENTION

Accordingly, one object of the present invention is to provide a process of producing methyl lactate in high yield and purity.

Another object of the present invention is to provide a method of synthesizing methyl lactate from readily available starting materials.

Yet another object of the present invention is to provide a method of preparing methyl lactate without using toxic materials or materials which require special handling procedures.

Briefly, these and other objects of the present invention as hereinafter will become more readily apparent can be obtained by a process for producing methyl lactate by (I) hydroformylating vinyl acetate or vinyl propionate with a gaseous mixture of hydrogen and carbon monoxide in an organic solvent in the presence of a substantially water-insoluble rhodium complex and a tri-substituted phosphine to form α-acetoxy- or propionyloxy-propionaldehyde, (II) subjecting at least a portion of the reaction mixture obtained in step (I) to extraction with an aqueous medium to obtain an aqueous layer containing α-acetoxy- or propionyloxy-propionaldehyde and an extraction residue containing the catalyst components, and recycling the extraction residue to the hydroformylation step (I), (III) separating α-acetoxy- or propionyloxy-propionaldehyde from the aqueous layer containing the same as obtained in step (II), (IV) oxidizing α-acetoxy- or propionyloxy-propionaldehyde obtained in step (III) in the liquid phase with oxygen gas or an oxygen-containing gas in the presence of an oxidation catalyst to form α-acetoxy- or propionyloxy-propionic acid, and (V) reacting α-acetoxy- or propionyloxy-propionic acid obtained in step (IV) with methanol in the presence of an acid catalyst, and recovering the resultant methyl lactate by distillation.

According to the process of the present invention, methyl lactate is produced in high purity and high yield. And the catalytic activity of the rhodium complex can be kept stable over a prolonged period of time, since the separation of α-acetoxypropionaldehyde or α-propionyloxypropionaldehyde and the rhodium complex from the reaction mixture obtained from the hydroformylation of vinyl acetate or vinyl propionate is accomplished by extraction with an aqueous medium. In addition, the process of the present invention has the following advantages: (i) excellent operational stability, (ii) ready availability of main raw materials, i.e., vinyl acetate or vinyl propionate, carbon monoxide, hydrogen and methanol, in quantities and at low costs, (iii) no special disposal requirements, and (iv) mild reaction conditions.

While methyl lactate, obtained by the process of the present invention, can be used as a solvent, it can also be hydrolyzed to lactic acid in high yield and high purity.

DETAILED DESCRIPTION OF THE INVENTION

In general terms the present invention provides a method of synthesizing methyl lactate by hydroformylating vinyl acetate or vinyl propionate to give α-acetoxy- or propionyl-propionaldehyde, oxidizing α-acetoxy- or propionyloxy-propionaldehyde to the corresponding α-acetoxy- or propionyloxy-propionic acid, and reacting this acid with methanol to give methyl lactate. The synthesis is shown by the following reaction sequence.

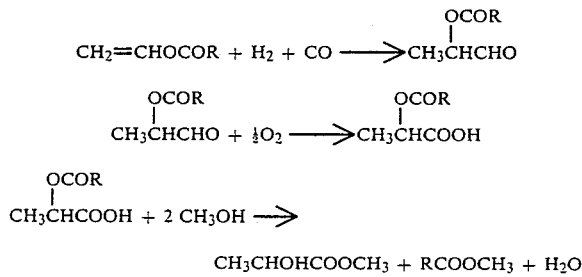

The rhodium complex used in the hydroformylation of vinyl acetate or propionyl acetate may be any desired rhodium complex that is capable of catalyzing the hydroformylation reaction under the reaction conditions used and is substantially insoluble in aqueous media. A number of rhodium complexes which meet these qualifications are known, and generally these known rhodium complexes can be employed for the purposes of the present invention. Suitable rhodium complexes include $HRh(CO)(PR_3)_3$, wherein R is an aryl group, $RhCl(PR_3)_3$, $Rh(acac)_3$, wherein acac is an acetylacetonyl group, $Rh(OAc)_3$, wherein OAc is an acetoxy group, $Rh_4(CO)_{12}$, $Rh_6(CO)_{16}$, $[Rh(CO)_2(PR_3)_2]_2$, $RhCl_3 \cdot 3H_2O$, $Rh_2O_3$, and the like. Among these compounds, rhodium compounds of the formula $HRh(CO)(PR_3)_3$ are especially desirable from the viewpoint of such considerations as catalytic activity, solubility, ease of handling, and the like. The rhodium complex is generally used in a concentration of 0.1 to 10 mmols per liter of the hydroformylation reaction mixture. The organic solvent used for the practice of the present invention should be a substantially water-insoluble solvent in order to facilitate the subsequent extraction of the reaction medium with an aqueous medium. Many organic solvents qualify in this regard, but when such physical and chemical properties are considered as the solubility of the catalyst components, the loss of the catalyst components due to dissolution into the aqueous layer, price, and possible influences on the subsequent separation step, it is advantageous to employ an aromatic hydrocarbon which may optionally be substituted by lower alkyl groups. For example, preferred solvents include benzene, toluene, xylene, ethylbenzene, and the like and substituted or unsubstituted, saturated alicyclic hydrocarbons such as cyclohexane, methylcyclohexane, and the like. The aforementioned tri-substituted phosphine compound is represented by the general formula PR'R"R''', wherein R' and R" are each an aromatic hydrocarbon group and, R''' is an aromatic hydrocarbon group or a saturated aliphatic hydrocarbon group of at least 3 carbon atoms. Examples of such tri-substituted phosphines are substituted or unsubstituted triarylphosphines, e.g., triphenylphosphine, tritolylphosphine, trinaphthylphosphine, and the like and diarylalkylphosphines such as diphenylpropylphosphine, diphenylhexylphosphine, and the like. Particularly preferred are substituted or unsubstituted triarylphosphines. The proper amount of such a tri-substituted phosphine is within the range of about 5 to about 50 moles per gram atom of rhodium and, more specifically, it is advantageous to employ the tri-substituted phosphine in a concentration of 10 to 150 millimoles per liter of the hydroformylation reaction mixture.

In the practice of the present invention, the hydroformylation of vinyl acetate or vinyl propionate is generally conducted at a temperature of 50° to 120° C., a carbon monoxide partial pressure of 4 to 50 kg/cm² (absolute), a reaction pressure of 25 to 150 kg/cm² and a molar hydrogen-to-carbon monoxide ratio of 0.5 to 5, the specific combination of conditions being selected with reference to the reaction temperature used, the desired selectivity for α-acetoxy- or propionyloxy-propionaldehyde, catalyst life, cost of equipment, and the like. The hydroformylation reaction can be carried out continuously or batchwise in a reaction vessel equipped with a stirrer or in a reactor of the bubble tower type, which is known per se. In order to inhibit a build-up of reaction heat, to improve the selectivity for α-acetoxy- or propionyloxy-propionaldehyde, and to prevent accumulation of high-boiling by-products, it is advantageous to feed vinyl acetate or vinyl propionate continuously into the reactor in such a manner that the concentration of vinyl acetate or vinyl propionate in the reaction system will be within a certain range. The concentration of α-acetoxy- or propionyloxy-propionaldehyde in the reaction mixture is preferably maintained in the range of about 0.5 to 3 moles per liter of the reaction mixture in view of such factors as the accumulation of high-boiling by-products, the loss of the rhodium complex and tri-substituted phosphine resulting from dissolution of the materials into the aqueous layer, the efficiency of extraction of α-acetoxy- or propionyloxy-propionaldehyde into the aqueous medium and so on.

The reaction mixture containing α-acetoxy- or propionyloxy-propionaldehyde, which is obtained by the hydroformylation of vinyl acetate or vinyl propionate (step (I)) is subjected to extraction with an aqueous medium in step (II), whereby α-acetoxy- or propionyloxy-propionaldehyde is dissolved into the aqueous phase. Suitable aqueous extraction media include water and aqueous solutions containing a small proportion (for example, about 5 to 10%) of the organic carboxylic acid derived from vinyl acetate or vinyl propionate. Suitable extraction equipment include any of the known extraction towers of the stirring vessel type, extraction towers of the RDC (rotary disk contractor) type, and perforated plate towers. However, an RDC extraction tower is most desirable from the point of view of the efficiency of extraction of α-acetoxy- or propionyloxy-propionaldehyde, losses of the rhodium complex and tri-substituted phosphine because of dissolution into the aqueous layer, and the like. A detailed investigation by the present inventors has shown that the degree of extraction of α-acetoxy- or propionyloxy-propionaldehyde into the aqueous layer and loss of the rhodium complex and tri-substituted phosphine resulting from dissolution in the aqueous layer are dependent on such factors as efficiency of contact between the aqueous medium and hydroformylation reaction mixture, extraction temperature, concentration of α-acetoxy- or propionyloxy-propionaldehyde in the reaction mixture, ratio by volume of the aqueous medium to the reaction mixture and the atmosphere at the time of extraction. Thus, a higher efficiency of contact between the aqueous medium and the hydroformylation reaction mixture, lower extraction temperatures and higher ratios by volume of the aqueous medium to the hydroformylation reaction mixture tend to promote the extent of extraction of α-acetoxy- or propionyloxy-propionaldehyde into the aqueous medium and reduce losses of the rhodium complex and tri-substituted phosphine resulting from dissolution of the materials into the aqueous layer. The extraction temperature is selected from the range from about 5° to 40° C. The volume ratio of the aqueous medium to the hydroformylation reaction mixture depends on the concentration of α-acetoxy- or propionyloxy-propionaldehyde in the reaction mixture. However, the ratio should preferably be selected within the range of 0.3–3 when said concentration is about 0.5 to 3 moles per liter of the reaction mixture. The extraction with an aqueous medium in step (II) is preferably conducted under an atmosphere of a substantially oxygen-free inert gas such as nitrogen, helium or argon, a gaseous mixture of hydrogen and carbon monoxide having a carbon monoxide partial pressure of at least 0.1 kg/cm$^2$, or a gaseous mixture of hydrogen and carbon monoxide diluted with one of the above-mentioned inert gases and having a carbon monoxide partial pressure of at least 0.1 kg/cm$^2$. In this manner, losses of the rhodium complex resulting from dissolution of materials into the aqueous layer can be minimized. While the extraction may be conducted in a batchwise fashion, a continuous process is prefered for commercial production purposes.

The extraction residue obtained in step (II), which contains the catalyst components, is returned to the hydroformylation step (I) for reuse. In this instance, a part of the extraction residue, after being subjected to a known catalyst activation treatment, if necessary, is recycled to the hydroformylation step.

In step (III), α-acetoxy- or propionyloxy-propionaldehyde is recovered from the aqueous layer obtained in step (II), which contains α-acetoxy- or propionyloxy-propionaldehyde. α-Acetoxy- or propionyloxy-propionaldehyde can be recovered as the distillate or distillation residue by heating the above-mentioned aqueous layer while maintaining the liquid phase temperature at about 90° C. or below. It has also been found that α-acetoxy- or propionyloxy-propionaldehyde can be separated extractively by an alternative method which comprises bringing the above-mentioned aqueous layer into contact with a carboxylic acid ester represented by formula (A)

$$C_nH_{2n+1}COOC_mH_{2m+1} \tag{A}$$

wherein n is an integer of 0 through 4, and m is an integer of 1 through 5, the sum of n and m being 3 through 5, or a dicarboxylic acid ester represented by formula (B)

$$ROOC(CH_2)_nCOOR' \tag{B}$$

wherein R and R' are each an alkyl group containing 2 or 3 carbon atoms and n is 0 or 1 or 2.

When a distillation method is employed, decreases in the purity and yield of α-acetoxy- or propionyloxy-propionaldehyde possibly caused by heating can be prevented by maintaining the liquid phase temperature at about 90° C. or below. In view of the subsequent oxidation reaction, it is desirable that the α-acetoxy- or propionyloxy-propionaldehyde should be as water-free as possible. However, when the water content is within permissible limits (generally 2 moles per mole of α-acetoxy- or propionyloxy-propionaldehyde), the water-containing α-acetoxy- or propionyloxy-propionaldehyde may be oxidized as it is. When an extraction method is employed, the extraction temperature is preferably about 5° C. to about 90° C., more preferably about 20° C. to about 80° C. When the degree of extraction of α-acetoxy- or propionyloxy-propionaldehyde tends to rise with increases in temperature, temperatures exceeding 90° C. are undesirable because portions of the α-acetoxy- or propionyloxy-propionaldehyde and the extracting solvent are hydrolyzed during the extraction procedure. The extraction may be carried out either continuously or batchwise. However, continuous extraction is industrially more advantageous.

Any extraction apparatus can be used such as a known stirring or perforated plate extraction tower. The carboxylic acid ester of formula (A), which is used as the extracting solvent, includes, among others, n-butyl formate, n-amyl formate, ethyl acetate, n-propyl acetate, isopropyl acetate, tert-butyl acetate, methyl propionate, ethyl propionate, methyl butyrate, methyl isobutyrate, and methyl valerate. Among these carboxylic acid esters, isopropyl acetate is especially preferred from the viewpoint of the extractability of α-acetoxy- or propionyloxy-propionaldehyde, the hydrolyzability, solubility in water and boiling point of the carboxylic acid ester, the composition of the azeotrope with water, the azeotropic point, and the solubility of water in the carboxylic acid ester, among others. When the carboxylic acid esters in which the sum of m and n in formula (A) is 2 or less, such as methyl acetate and ethyl formate, are used as the extracting solvents, α-acetoxy- or propionyloxy-propionaldehyde can easily be extracted into the solvents. However, at the same time, water is readily extracted into the solvents, so that efficient extraction of α-acetoxy- or propionyloxy-propionaldehyde cannot be achieved. The use of those carboxylic acid esters in which the sum of m and n in formula (A) is 6 or more such as n-butyl caprate as the extracting solvent, is disadvantageous from the industrial standpoint because α-acetoxy- or propionyloxy-propionaldehyde is barely extracted with the solvents. In this instance, some solvents have boiling points close to the boiling point of the extracted α-acetoxy- or propionyloxy-propionaldehyde and therefore precision distillation becomes necessary for isolation of these materials from each other in the subsequent step.

Suitable examples of the dicarboxylic acid ester of general formula (B) include diethyl oxalate, diisopropyl oxalate, ethyl isopropyl oxalate, diethyl malonate and diethyl succinate. Among these dicarboxylic acid esters, diethyl oxalate and diethyl malonate are especially preferred from the viewpoint of extractability of α-acetoxy-or propionyloxy-propionaldehyde, the hydrolyzability, solubility in water and boiling point of the dicarboxylic acid esters, the solubility of water in the dicarboxylic acid esters, other physical properties, the generality of use and the prices of the solvents, among others. When those dicarboxylic acid esters of formula (B), wherein n is an integer of 0 to 2 and each of R and R' is methyl, such as dimethyl succinate, are used as the extracting solvent, α-acetoxy- or propionyloxy-propionaldehyde can easily be extracted into the solvents but at the same time water is readily soluble in the solvents, so that efficient extractive separation of α-acetoxy- or propionyloxy-propionaldehyde cannot be attained. The use of those dicarboxylic acid esters of formula (B), wherein n is an integer of 3 or more, such ad di n-butyl adipate, is disadvantageous from the industrial standpoint because α-acetoxy- or propionyloxy-propionaldehyde is barely extracted with such solvents, and/or the boiling points thereof are too high. When those dicarboxylic acid esters of formula (B), wherein is an integer of 3 or more and R and R' are each an alkyl group containing 2 or 3 carbon atoms are used as the extracting solvent, a prolonged period of time is required for phase separation because the specific gravities of the solvents are very close to the specific gravity of water. For most practical purposes from about 0.5 to about 5 volumes of the carboxylic acid ester of formula (A) or the dicarboxylic acid ester of formula (B) are used per volume of the aqueous solution containing α-acetoxy- or propionyloxy-propionaldehyde. The extraction residue can be returned to step (II) as it is for reuse as the aqueous medium. α-Acetoxy- or propionyloxy-propionaldehyde can be separated from the extract layer by a conventional distillation procedure. When the extracting solvent is a carboxylic acid ester of formula (A), water and the extracting solvent are distilled off in the form of an azeotropic mixture and then the extracting solvent is removed by distillation and α-acetoxy- or propionyloxy-propionaldehyde is recovered as the distillation residue. When the extracting solvent is a dicarboxylic acid ester of formula (B), α-acetoxy- or propionyloxy-propionaldehyde is recovered as a distillate after water and a small amount of acetic or propionic acid present in the extract layer have been removed by distillation. In this instance, maintenance of the distillation temperature at 120° C. or below, if necessary with adequate adjustment of the degree of reduction in pressure, is important for high yield recovery of highly pure α-acetoxy- or propionyloxy-propionaldehyde, since α-acetoxy- or propionyloxy-propionaldehyde is relatively low in thermal stability.

In step (IV), the α-acetoxypropionaldehyde or α-propionyloxypropionaldehyde obtained in step (III) is oxidized with gaseous oxygen or an oxygen-containing gas in the presence of an oxidation catalyst. Suitable oxidation catalysts include copper salts, iron salt, nickel salts, cobalt salts, manganese salts, and the like. From the viewpoint of selectivity of reaction, copper salts, iron salts and nickel salts are preferred. Examples of the oxidation catalyst are cuprous halides, cupric halides, cuprous carboxylates, cupric carboxylates, cuprous sulfate, cupric sulfate, cupric nitrate, ferrous halides, ferric halides, ferrous carboxylates, ferric carboxylates, ferric sulfate, nickel carboxylates, nickel sulfate, nickel halides, cobaltous carboxylates, cobaltous sulfate, manganeous carboxylates, and manganous sulfate. Among these, cupric carboxylates, ferrous carboxylates, ferric carboxylates and nickel carboxylates are especially preferred from the viewpoints of solubility of the catalysts in the reaction mixture, catalytic activity, and corrosiveness to reaction apparatus, among others. The salt-forming carboxylic acids may include lower carboxylic acids such as acetic acid, propionic acid and butyric acid. These metal salts may be used either alone or in combination in amounts of two or more. The metal salt is used in an amount of 0.1 to 50 millimoles per liter of reaction mixture when it is a copper, iron or nickel salt, and in an amount of 0.01 to 1.0 millimole per liter of reaction mixture when it is a cobalt or manganese salt. The reaction is carried out at a pressure of 1 to about 20 atmospheres (absolute) and a temperature of 40°–100° C. in a stirring vessel type reactor or bubble tower type reactor while passing gaseous oxygen, air or mixed gas containing nitrogen and oxygen in an arbitrary ratio therethrough. Suitable solvents for reaction include acetic acid, propionic acid, methyl acetate, α-acetoxy- or propionyloxy-propionic acid, arbitrary mixtures of these acids, and the like. Among them, α-acetoxy- or propionyloxy-propionic acid, which is the reaction product and at the same time can serve as the solvent, is most preferable when the subsequent step is considered. When α-acetoxy- or propionyloxy-propionic acid is used as the solvent, small amounts of acetic acid, for instance, may be present therein without causing any problems. Since this reaction is very exothermic like the oxidation of common aldehydes with oxygen, control of the reaction temperature is required. Therefore, the reaction is conducted while maintaining the aldehyde concentration in the reaction mixture at a low level by adding α-acetoxy- or propionyloxy-propionaldehyde continuously or intermittently to the reaction medium.

The α-acetoxypropionic acid or α-propionyloxy-propionic acid formed in step (IV), without isolation from the reaction mixture by distillation, is reacted wih methanol in the presence of an acid catalyst so that it is converted to methyl lactate (step (V)). By subjecting thermally unstable α-acetoxy- or propionyloxy-propionic acid to the reaction without separating the same by distillation, thermal decomposition of α-acetoxy- or propionyloxy-propionic acid can be suppressed. If unreacted α-acetoxy- or propionyloxy-propionaldehyde is present in the reaction mixture of step (V), it reacts with methanol leading to the formation of lactaldehyde and acetol as by-products. Therefore, the oxidation reaction in step (IV) should preferably be as complete as possible. The acid catalyst is, for example, sulfuric acid, phosphoric acid, benzenesulfonic acid, p-toluenesulfonic acid, or the proton form of an ion exchange resin. The acid catalyst is used in an amount equivalent to 1 to 1,000 milliequivalents of proton per liter of the reaction mixture. Methanol is used in an amount of 3–7 moles per mole of α-acetoxy- or propionyloxy-propionic acid. The reaction temperature should be within the range of 50°–150° C. The reactor type depends on the form of the acid catalyst used. When the catalyst exists as a liquid in the reaction system, the reaction is conducted in a stirring vessel type reactor. When an ion exchange resin is used, it is performed in a stirring vessel type reactor or in a column packed with the ion exchange resin. In the most preferred mode of practice, methanol and α-acetoxy- or propionyloxy-propionic acid are fed continuously or intermittently to a reaction medium containing the acid catalyst while the product methyl lactate is distilled from the reaction system. When carried out in this manner, the reaction gives methyl lactate in an improved yield with savings in utilities. The distillate contains not only methyl lactate but also methyl acetate or methyl propionate, water, methyl α-acetoxy- or propionyloxy-propionate and unreacted methanol. The distillate can be separated into respective fractions by conventional distillation or by passing it in the gaseous state to a distilling column for treatment. Furthermore, methyl lactate may also be recovered from the reaction mixture by distillation. The methyl α-acetoxy- or propionyloxy-propionate separated may be returned to step (V) for reuse in the reaction.

Having generally described this invention, a further understanding can be obtained by reference to certain specific examples which are provided herein for purpose of illustration only and are not intended to be limiting unless otherwise specified.

EXAMPLE 1

(i) Synthesis of α-acetoxypropionaldehyde and separation of the same from reaction mixture The synthesis of α-acetoxypropionaldehyde and extraction of this material with water were conducted in the apparatus described below. The whole procedure was performed under conditions which excluded the entry of air into the system as much as possible and distilled water and toluene were used after displacement and removal of dissolved oxygen with nitrogen gas.

Reactor: A one-liter stainless steel autoclave equipped with thermometer, stirrer, liquid feed pump, liquid sampling outlet, gas inlet and gas outlet was used.

Extractor: A one-liter four-necked flask equipped with thermometer, stirrer, liquid feed inlet, liquid sampling outlet, gas inlet and gas outlet was used as the extractor. The extractor was connected to the above-mentioned autoclave by a pipe.

A solution of 918 mg (1.0 millimole) of HRh(CO)[P(C$_6$H$_5$)$_3$]$_3$ and 2,620 mg (10 millimoles) or triphenylphosphine in 420 ml of toluene was washed with two 420-ml portions of distilled water at room temperature in an atmosphere of a mixed gas composed of hydrogen and carbon monoxide (H$_2$/CO mole ratio 2/1) and charged into the above-mentioned autoclave. The atmosphere within the autoclave was replaced with a hydrogen-carbon monoxide mixture (H$_2$/CO mole ratio 2/1). The autoclave was then pressurized to 30 kg/cm$^2$ (gauge) with the same gas mixture as above and heated in an oil bath so that the inside temperature was maintained constantly at 70° C. Stirring was started at the rate of 600 rpm (revolutions per minute), and 71 g (830 millimoles) of vinyl acetate was introduced continuously over 1.5 hours. The off-gas flow rate was adjusted to 20 liters per hour. In this manner, the reaction was conducted at 70° C. and 30 kg/cm$^2$ (gauge) with stirring. Low boiling compounds (vinyl acetate, propionaldehyde, toluene, etc.) present in the off-gas were collected in a trap placed in a dry ice-acetone bath. After completion of the feeding of vinyl acetate starting material, stirring was continued under the same conditions for 2 hours as to allow the reaction to proceed further. Analysis of the reaction mixture by gas chromatography revealed that the conversion of vinyl acetate in 3.5 hours amounted to 90% and the selectivity toward α-acetoxypropionaldehyde was 95% based on the converted vinyl acetate. The reaction mixture was cooled to room temperature and then transferred by taking advantage of the internal pressure of the reactor to the above-mentioned extractor in which the atmosphere had been replaced with a hydrogen-carbon monoxide mixture (H$_2$/CO mole ratio 2/1). The extractor was further charged with 125 ml of nitrogen-purged distilled water, and the extraction of α-acetoxypropionaldehyde from the toluene solution (reaction mixture) with water was effected by stirring the solution at the rate of 500 rpm at 20° C. for 20 minutes. The aqueous layer which formed upon standing was removed from the system, and 125 ml of distilled water was added to the remaining toluene solution and the extraction was again conducted under the same conditions (total water/reaction mixture volume ratio=½). These two extraction procedures transferred 95% of the α-acetoxypropionaldehyde to the aqueous layer. The concentration of rhodium in the aqueous layer (as determined by atomic absorption spectrometry) was 0.05 ppm and that of phosphorus compound (as determined by colorimetry) was 2 ppm as phosphorus. The extraction residue, namely the solution containing the catalyst components, was transferred to the above-mentioned autoclave by taking advantage of the pressure of the hydrogen-carbon monoxide mixture. Vinyl acetate was added continuously at the rate of 48 g/hr for 80 minutes with stirring under the conditions of 70° C., 30 kg/cm$^2$ (gauge) and 600 rpm. Thereafter, the reaction was allowed to proceed further by stirring the solution for 2 hours. Then, the reaction mixture was subjected to extraction with water by following the same procedure under the same conditions described above. The extraction residue was again fed under pressure to the autoclave and the hydroformylation of vinyl acetate was conducted. In this manner, the hydroformylation of vinyl acetate followed by extraction with water was repeated 10 times in all. As a result, about 3.2 liters total of the aqueous extract layer was obtained. The conversions of vinyl acetate in the 3rd, 6th and 10th runs were 91%, 90% and 91%, respectively, and the concentrations of rhodium in the aqueous extract layer were 0.05 ppm, 0.06 ppm and 0.06 ppm (as rhodium), respectively. These conversion and concentration values did not show any substantial change throughout the repeated runs. The aqueous extract layer in each run was stored at 5° C. under a nitrogen atmosphere.

(ii) Separation of α-acetoxypropionaldehyde from the aqueous extract layer

A glass reduced pressure distillation apparatus preliminarily purged with nitrogen gas was charged with 500 ml of the aqueous extract layer obtained in the repeated runs mentioned above under (i), i.e., an aqueous solution containing about 2 moles of α-acetoxypropionaldehyde per liter. While maintaining the liquid phase temperature at 60°–65° C. and by varying the degree of reduction in pressure, fractional distillation was conducted for about 2 hours. In this manner, 115 g of α-acetoxypropionaldehyde containing about 8 weight percent of water was obtained. No impurities other than water and a small amount of acetic acid were detected in the α-acetoxypropionaldehyde fraction. The fractional distillation procedure for α-acetoxypropionaldehyde was repeated five more times in the same manner as described above using 500-ml portions of the remaining aqueous extract layer. The distillation yield of α-acetoxypropionaldehyde in each fractional distillation run was 90–95%, and almost no high-boiling by-products were detected in each distillation residue (bottoms). The α-acetoxypropionaldehyde which was separated was stored at 5° C. under a nitrogen atmosphere.

(iii) Synthesis of α-acetoxypropionic acid

A 300-ml four-necked flask equipped with thermometer, stirrer, reflux condenser, liquid measuring feed pump, gas inlet and gas outlet was charged with 12.5 mg (0.05 millimole) of nickel acetate tetrahydrate and 50 ml of a solution of α-acetoxy-propionic acid containing 8 weight percent water which had been separately synthesized. The contents of the flask were stirred until the temperature thereof reached 55° C. and dissolution of the nickel acetate was complete. Thereafter, oxygen gas was blown into the flask at the rate of 10 liters/hr and stirring was started at the rate of 800 rpm at 55° C. The oxidation of α-acetoxypropionaldehyde was conducted by continuously feeding the α-acetoxypropionaldehyde containing 8 weight percent water obtained by the above-mentioned distillation separation procedure, at the rate of 12 ml/hr over 8 hours by means of the liquid measuring feed pump. After 8 hours, feeding of α-acetoxypropionaldehyde was discontinued, and stirring was continued at the rate of 800 rpm and at the temperature of 55° C. for 2 more hours so as to allow the reaction to proceed further. The conversion of α-acetoxypropionaldehyde at the time the feeding of α-acetoxypropionaldehyde was discontinued (8 hours after start of the reaction) and at the time the reaction was finished (10 hours after start of the reaction) were estimated by gas chromatography at 85% and 98%, respectively. Determination by gas chromatography of the concentration of carbon dioxide in the off-gas revealed that the yield of carbon dioxide was 3% based on the converted α-acetoxypropionaldehyde. The reaction mixture was charged into a 200 ml reactor equipped with a thermometer, an oxygen gas inlet (at the reactor bottom) and an off-gas outlet, and heated in an oil bath until the contents reached and were maintained at a constant temperature of 80° C. While introducing oxygen gas through the oxygen gas inlet at the rate of 3 liters/hr, the reactor contents were maintained at 80° C. for 1.5 hours. After 1.5 hours of reaction, the reaction mixture was analyzed by gas chromatography, which showed that the conversion of α-acetoxypropionaldehyde was not less than 99.5%. After cooling to room temperature, the reaction mixture was sampled and the sample was analyzed by iodometry for active oxygen content. Said content was 0.01%. Using the remaining portion of α-acetoxypropionaldehyde, the same oxidation procedure was repeated five more times under the same conditions. The mean conversion of α-acetoxypropionaldehyde at the time when the reaction was finished (i.e., 10 hours after start of the reaction) was 98%, and that of α-acetoxypropionaldehyde after a lapse of 1.5 hours while maintaining the internal temperature at 80° C. was not less than 99.5%.

(iv) Synthesis of methyl lactate

A 100-ml four-necked flask equipped with thermometer, stirrer, nitrogen gas inlet and outlet, liquid measuring feed pump (with feed pipe connected to the bottom of flask) and a distillate collector connected to a cooler was charged with 10 ml of the α-acetoxypropionaldehyde oxidation mixture obtained by the above procedure (iii) and 150 mg of 97% sulfuric acid. While introducing nitrogen gas slowly, the flask was immersed in an oil bath adjusted to 145° C. When the inside temperature exceeded 100° C., continuous introduction of a preheated (40°–50° C.) mixture of the α-acetoxypropionaldehyde oxidation mixture and methanol (methanol/reaction mixture weight ratio = 17/20) was started at the rate of 28 ml/hr with stirring at the rate of 700 rpm. Immediately after the start of the introduction of the liquid mixture, a distillate composed of methyl acetate, methanol, water, methyl lactate and methyl α-acetoxypropionate began to be discharged. The reaction was carried out continuously under these conditions for 15 hours. The volume of the liquid within the reactor remained almost constant throughout the reaction period. However, the liquid volume was minutely adjusted occasionally by keeping the flask apart from the oil bath for a short period of time or by stopping the feeding of the charged liquid for a while. Analysis of the distillate (about 400 ml) by gas chromatography and Karl-Fischer determination indicated that it contained the following compounds: Methanol, 93.6 g; methyl acetate, 92.6 g; water, 39.2 g; methyl lactate, 127.2 g; methyl α-acetoxypropionate, 24.0 g; methyl methoxylacetate 0.48 g. From the above data, the yield of methyl lactate was calculated at 87% based on the charged α-acetoxypropionic acid. Analysis by gas chromatography revealed that only a trace amount of carbon monoxide had formed as a by-product.

(v) Separation of methyl lactate from the reaction mixture

A distillation apparatus including a packed column with the theoretical plate number of 20 was charged with 375 ml of the distillate obtained by the procedure mentioned above under (iv). In the first place, fractional distillation was conducted under atmospheric pressure which caused methyl acetate and methanol to distill off almost completely. Then, fractional distillation was continued under a pressure of 70 mmHg. Eventually about 90 g of methyl lactate was obtained as the main fraction boiling at 75°–77° C. The methyl lactate recovered contained no impurities detectable by gas chromatography, was colorless and transparent.

EXAMPLE 2

The procedure described under section (i) in Example 1 was followed except that 80 g (800 millimoles) of vinyl propionate and 3,040 mg (10 millimoles) of tritolylphosphine were used in place of vinyl acetate and triphenylphosphine, respectively and that 500 ml of distilled water purged with nitrogen was used as the solvent for extraction (total water/reaction mixture volume ratio = 1/1). Hydroformylation of vinyl propionate followed by extraction with water was carried out repeatedly ten times in all. As a result, a total of about 5.7 liters of an aqueous extract layer was obtained. The conversion of vinyl propionate, the selectivity toward α-propionyloxypropionaldehyde, the rate of recovery by extraction of α-propionyloxypropionaldehyde and concentration of rhodium in the aqueous extract layer were on the average 88%, 92%, 90% and 0.03 ppm, respectively.

The same reduced pressure distillation apparatus as used in Example 1 (section (ii)) was charged with 500 ml of the aqueous extract layer (aqueous solution containing about 1 mole/liter of α-propionyloxypropionaldehyde) and fractional distillation was effected under reduced pressure for about 2 hours while maintaining the liquid phase temperature at 75° C. A 63 g amount of α-propionyloxypropionaldehyde containing about 5 weight percent of water was obtained. In the same manner, eight 500-ml portions of the remaining aqueous extract layer were fractionated under the same conditions as above. The mean rate of recovery by distillation was 90%.

An α-propionyloxypropionic acid solution (50 ml) containing 5 weight percent of water and the nickel catalyst were prepared separately, and the oxidation of α-propionyloxypropionaldehyde was conducted repeatedly four times in all by the same procedure as mentioned under section (iii) in Example 1 except that the α-propionyloxypropionaldehyde obtained by the above-mentioned fractional distillation procedure and containing 5 weight percent of water was fed continuously at the rate of 13 ml/hr. The mean conversion of α-propionyloxypropionaldehyde and the mean yield of carbon dioxide at the time of finishing the reaction (10 hours after start of the reaction) were 97%, and 4% based on the converted α-propionyloxypropionaldehyde, respectively.

The mean conversion of α-propionyloxypropionaldehyde after being held at an internal temperature at 80° C. for 1.5 hours was not less than 99.5%. The methyl lactate synthesis was conducted by the same procedure as described under section (iv) in Example 1 except that a mixture of the thus-obtained α-propionyloxypropionaldehyde oxidation reaction mixture and methanol (methanol/reaction mixture weight ratio = 1/1) was fed continuously at the rate of 25 ml/hr. The yield of methyl lactate was 88% based on the charged α-propionyloxypropionic acid. The total distillate containing methyl lactate was charged into the distillation apparatus as mentioned under section (v) in Example 1 and subjected to fractional distillation for recovery of methyl lactate. Eventually there was obtained about 75 g of a methyl lactate fraction boiling at 75°–77° C./70 mmHg.

EXAMPLE 3

The procedure of section (i) in Example 1 was repeated five times to give a total of about 1.6 liters of an aqueous extract layer. The reduced pressure distillation apparatus as used in the procedure of section (ii) in Example 1 was charged with 500 ml of the aqueous extract layer, and water and acetic acid were removed by distillation over 2 hours while maintaining the liquid phase temperature at 70° C. and varying the degree of reduction in pressure. A distillation residue of 105 g of α-acetoxypropionaldehyde containing 3 weight % of water and a very small amount of acetic acid were obtained. Using 500-ml portions of the remaining aqueous extract layer, the same procedure was repeated two more times, and about 100 g per run of α-acetoxypropionaldehyde, which contained on an average about 3 weight % of water and a very small amount of acetic acid, was recovered as the distillation residue.

A catalyst solution was prepared by dissolving 26 mg (0.15 millimole) of ferrous acetate in 50 ml of α-acetoxypropionic acid synthesized separately, and the oxidation of α-acetoxypropionaldehyde was repeated 2 times in all by following the procedure described under section (iii) in Example 1 except that the α-acetoxypropionaldehyde containing 3 weight % of water was fed at the rate of 11 ml/hr into the reaction zone at the reaction temperature of 65° C. The mean conversion of α-acetoxypropionaldehyde and the mean yield of carbon dioxide at the time of conclusion of the reaction (i.e. 10 hours after start of the reaction) were 96% and 2.5%, respectively. The mean conversion after 1.5 hours of maintenance of the inside temperature at 80° C. was 99%. The methyl lactate synthesis was performed by following the procedure mentioned under section (iv) in Example 1 except that a mixture of the thus obtained α-acetoxypropionaldehyde oxidation reaction mixture and methanol (methanol/reaction mixture weight ratio = 8/7) was fed into the reactor continuously at the rate of 22 ml/hr. The yield of methyl lactate was 90% based on the α-acetoxypropionic acid charged. The total distillate containing methyl lactate was charged into the same distillation apparatus as used in section (v) of Example 1, and fractional distillation of methyl lactate was performed in the same manner as described in the Example to eventually give about 76 g of a methyl lactate fraction boiling at 75°–77° C./70 mmHg.

EXAMPLE 4

The procedure described in section (i) in Example 1 for hydroformylation of vinyl acetate followed by extraction with water was repeated 6 times in all under the same conditions except that 88 ml of distilled water was used for each extraction run (total water/reaction mixture volume ratio = 0.35/1), to give about 1.4 liters in total of an aqueous solution containing about 2.7 moles/liter of α-acetoxypropionaldehyde and a small amount of acetic acid and propionaldehyde. A one-liter glass extractor equipped with a stirrer, a reflux condenser and a thermometer preliminarily purged with nitrogen gas was charged under nitrogen with 240 ml of the above-mentioned aqueous extract layer and 480 ml of isopropyl acetate purged with nitrogen gas, and the extraction was effected by stirring at the rate of 500 rpm at the temperature of 60° C. for 30 minutes. This extraction procedure resulted in the transfer of 78% of the α-acetoxypropionaldehyde in the aqueous solution into the isopropyl acetate layer. The amount of water in the isopropyl acetate layer was about 20 g. The isopropyl acetate layer obtained by the above procedure was transferred to a distillation apparatus which had been purged with nitrogen gas, and while maintaining the liquid phase temperature at 100° C. or below, first the remaining propionaldehyde and then water were distilled off as azeotropes with isopropyl acetate under atmospheric pressure, and thereafter the isopropyl acetate was distilled off under reduced pressure. About 55 g of α-acetoxypropionaldehyde containing only a trace amount of acetic acid was obtained as the bottom liquid. Using 240-ml portions of the remaining aqueous extract layer, the same procedure as above was repeated four more times to give about 55 g per run of α-acetoxypropionaldehyde containing a trace amount of acetic acid as the bottom liquid.

A catalyst solution was prepared by dissolving 26 mg (0.15 millimole) of ferrous acetate in 50 ml of α-acetoxypropionic acid synthesized separately, and the oxidation of α-acetoxypropionaldehyde was repeated two times in all by the same procedure as described in section (iii) in Example 1 except that the rate of addition of α-acetoxypropionaldehyde and the mean yield of carbon dioxide at the time of finishing the reaction (i.e. 10 hours after the start of the reaction) were 97% and 1.5%, respectively. The mean conversion of α-acetoxypropionaldehyde after 1.5 hours of maintenance at 80° C. (inside temperature) was 99.5% or more. The methyl lactate synthesis was performed by the same procedure as mentioned in section (iv) in Example 1 except that a mixture of the thus obtained α-acetoxypropionaldehyde oxidation reaction mixture and methanol (methanol/reaction mixture weight ratio = 1/1) was fed continuously at the rate of 20 ml per hour. The yield of methyl lactate was 92% based on the charged α-acetoxypropionic acid. The total distillate containing methyl lactate was charged into the same distillation apparatus as described in section (v) in Example 1 and subjected to fractional distillation under the same conditions as described previously for recovery of methyl lactate. About 90 g of a methyl lactate fraction boiling at 75°–77° C./70 mmHg was eventually obtained.

EXAMPLES 5-8

The synthesis of methyl lactate by the described series of reactions starting with vinyl acetate was conducted under the same conditions as described in Example 4 except that various monocarboxylic acid esters were used in place of isopropyl acetate at different extraction temperatures. The results of extraction of α-acetoxypropionaldehyde with a variety of monocarboxylic acid esters are shown in Table 1.

TABLE 1

Extraction of α-acetoxypropionaldehyde with various monocarboxylic acid esters

| Example | Extraction solvent | Extraction temperature (°C.) | % Recovery of APA* (%) |
| --- | --- | --- | --- |
| 5 | n-Propyl acetate | 60 | 76 |
| 6 | n-Butyl formate | 60 | 75 |
| 7 | Ethyl propionate | 70 | 77 |
| 8 | tert-Butyl acetate | 70 | 74 |

*APA: α-Acetoxypropionaldehyde

In each Example, fractional distillation of the monocarboxylic acid ester layer gave, after distilling off water and the monocarboxylic acid ester, 50–55 g per run of α-acetoxypropionaldehyde containing only a trace amount of acetic acid as the bottom liquid. The oxidation of α-acetoxypropionaldehyde (two times), methanolysis of α-acetoxypropionic acid and fractional distillation of methyl lactate conducted under the same conditions as mentioned above eventually gave 80–90 g of a methyl lactate fraction boiling at 75–77° C./70 mmHg.

EXAMPLE 9

The procedure for hydroformylation of vinyl acetate and the subsequent extraction with water was repeated six times in all under the same conditions as described under section (i) in Example 1 except that 100 ml per run of distilled water was used for the extraction purpose (total water/reaction mixture volume ratio=0.4/1). About 1.6 liters of an aqueous solution containing about 2.5 moles/liter of α-acetoxypropionaldehyde and small amounts of acetic acid and propionaldehyde were obtained. A one-liter glass extractor equipped with stirrer and thermometer was purged with nitrogen gas and then charged, under nitrogen, with 250 ml of the aqueous extract layer and 500 ml of diethyl oxalate purged with nitrogen gas, and the extraction was effected by stirring the solution at a temperature of 60° C. and at the rate of 500 rpm for 30 minutes. This extraction procedure transferred 81% of the α-acetoxypropionaldehyde to the diethyl oxalate layer. The diethyl oxalate layer contained about 17 g of water. The diethyl oxalate layer obtained by the above procedure was transferred to a distillation apparatus which had been purged with nitrogen, and water, acetic acid and α-acetoxypropionaldehyde were separated by distillation under reduced pressure while maintaining the liquid phase temperature at 100° C. or below. After removal of water and acetic acid by distillation, about 50 g of an α-acetoxypropionaldehyde fraction containing trace amounts of water and acetic acid was recovered. Using 250-ml portions of the remaining aqueous extract layer, the same procedure was repeated five more times to give about 50 g per run of an α-acetoxypropionaldehyde fraction containing trace amounts of water and acetic acid.

A catalyst solution was prepared by dissolving 35 mg (0.20 millimole) of ferrous acetate in 50 ml of α-acetoxypropionic acid synthesized separately, and the α-acetoxypropionaldehyde oxidation reaction was conducted two times in all by the procedure described in section (iii) in Example 1 except that the α-acetoxypropionaldehyde was fed at the rate of 12 ml/hr at the reaction temperature of 65° C. The mean conversion of α-acetoxypropionaldehyde and the mean yield of carbon dioxide at the time the reaction was finished (10 hours after the start of the reaction) were 95% and 2%, respectively. The mean rate of conversion at the time after 1.5 hours of maintenance of the internal temperature at 80° C. was not less than 99%. The methyl lactate synthesis was conducted by the procedure described in section (iv) in Example 1 except that a mixture of the thus-obtained α-acetoxypropionaldehyde oxidation reaction mixture and methanol (methanol/reaction mixture weight ratio=1/1) was fed continuously at the rate of 20 ml/hr. The yield of methyl lactate was 90% based on the charged α-acetoxypropionic acid. The total distillate containing methyl lactate was charged into the same distillation apparatus as described in section (v) in Example 1 and subjected to fractional distillation for recovery of methyl lactate. Eventually there was obtained about 85 g of methyl lactate fraction boiling at 75–77° C./70 mmHg.

EXAMPLES 10-12

The synthesis of methyl lactate by the described series of reactions starting from vinyl acetate was conducted under the same conditions as described in Example 9 except that various dicarboxylic acid esters were used in place of diethyl oxalate at different extraction temperatures. The results of extraction of α-acetoxypropionaldehyde with a variety of dicarboxylic acid esters are shown in Table 2.

TABLE 2

Extraction of α-acetoxypropionaldehyde with various dicarboxylic acid esters

| Example | Extraction solvent | Extraction temperature (°C.) | % Recovery of APA (%) |
| --- | --- | --- | --- |
| 10 | Diethyl succinate | 60 | 84 |
| 11 | Diethyl malonate | 60 | 82 |
| 12 | Diethyl oxalate | 50 | 76 |

In each example, fractional distillation of the diccarboxylic acid ester layer gave, after removing water and acetic acid by distillation, 45–50 g per run of an α-acetoxypropionaldehyde fraction, which contained only trace amounts of water and acetic acid. The oxidation of α-acetoxypropionaldehyde (two times), methanolysis of α-acetoxypropionic acid and fractional distillation for recovery of methyl lactate were conducted under the same conditions to eventually give 80–90 g of a methyl lactate fraction boiling at 75–77° C./70 mmHg.

Having now fully described this invention, it will be apparent to one of ordinary skill in the art that many changes and modifications can be made thereto without departing from the spirit or scope of the invention as set forth herein.

What is claimed as new and is intended to be secured by Letters Patent of the United States is:

1. A process for producing methyl lactate, which comprises the steps of:
   (I) hydroformylating vinyl acetate or vinyl propionate with a gaseous mixture of hydrogen and carbon monoxide in an organic solvent in the presence of a substantially water-insoluble rhodium complex and a trisubstituted phosphine to form α-acetoxy- or propionyloxypropionaldehyde; '(II) extracting the reaction mixture obtained in step (I) with an aqueous medium, thereby obtaining an aqueous layer contaning α-acetoxy- or propionyloxy-propionaldehyde and an extraction residue containing the catalyst components, and recycling the extraction residue to the hydroformylation step (I);
   (III) separating α-acetoxy- or propionyloxy-propionaldehyde from the aqueous layer containing the same as obtained in step (II);
   (IV) oxidizing α-acetoxy- or propionyloxy-propionaldehyde obtained in step (III) in the liquid phase with oxygen gas or an oxygen-containing gas in the presence of an oxidation catalyst to form α-acetoxy- or propionyloxy-propionic acid; and
   (V) reacting α-acetoxy- or propionyloxy-propionic acid obtained in step (IV) with methanol in the presence of an acid catalyst, and recovering the resultant methyl lactate by distillation.

2. The process of claim 1, wherein the hydroformylation reaction of vinyl acetate or vinyl propionate in step (I) is conducted at a reaction temperature of 50° to 120° C., an absolute carbon monoxide partial pressure of 4 to 50 kg/cm², a reaction pressure of 25 to 150 kg/cm², with the molar ratio of hydrogen to carbon monoxide being 0.5 to 5.

3. The process of claim 1, wherein the extraction procedure of the step (II) is conducted at a temperature of about 5° to b 40° C. under an atmosphere which is either an inert gas, a hydrogen-carbon monoxide gas mixture having a carbon monoxide partial pressure of at least 0.1 kg/cm², or a hydrogen-carbon monoxide gas mixture diluted with said inert gas and having a carbon monoxide partial pressure of at least 0.1 kg/cm².

4. The process of claim 1, wherein α-acetoxy- or propionyloxy-propionaldehyde is separated as a distillate or a distillation residue from the aqueous layer obtained froms step (II) by heating said aqueous layer while maintaining the liquid phase temperature at about 90° C. or below.

5. The process of claim 1, wherein the aqueous layer obtained in step (II) is subjected to extraction with a carboxylic acid ester of formula (A):

$$C_nH_{2n+1}COOC_mH_{2m+1} \qquad (A)$$

wherein n is an integer of 0 to 4; m is an integer of 1 to 5; and the sum of n and m is 3 to 5, and the resulting extract layer is subjected to distillation for the removal of water and the extracting solvent therefrom, whereby α-acteoxy- or propionyloxy-propionaldehyde is recovered as a distillation residue.

6. The process of claim 1, wherein the aqueous layer obtained in step (II) is subjected to extraction with a dicarboxylic acid ester of formula (B):

$$ROOC(CH_2)_nCOOR' \qquad (B)$$

wherein R and R' each is an alkyl group of 2 to 3 carbon atoms; and n is an integer of 0 to 2, and the resulting extract layer is subjected to distillation, whereby α-acetoxy- or propionyloxy-propionaldehyde is recovered as a distillate.

7. The process of claim 1, wherein the oxidation of α-acetoxy- or propionyloxy-propionaldehyde in step (IV) is conducted at a reaction pressure of 1 to about 20 atmospheres (absolute) and a reaction temperature of 40° to 100° C.

8. The process of claim 1, wherein the oxidation catalyst is a copper salt, iron salt, nickel salt, cobalt salt or manganese salt.

9. The process of claim 1, wherein the reaction of α-acetoxy- or propionyloxy-propionic acid with methanol in step (IV) is conducted at a reaction temperature of 50° to 150° C.

10. The process of claim 1, wherein the acid catalyst is sulfuring acid, phosphoric acid, benzenesulfonic aicd, p-toluenesulfonic acid or an ion exchange resin in proton form.

* * * * *